US005571510A

United States Patent [19]
Nobori et al.

[11] Patent Number: 5,571,510
[45] Date of Patent: Nov. 5, 1996

[54] METHOD FOR SELECTIVE METHIONINE STARVATION OF MALIGNANT CELLS IN MAMMALS

[75] Inventors: Tsutomu Nobori; Dennis A. Carson, both of San Diego, Calif.

[73] Assignee: The Regents of the University of California

[21] Appl. No.: 176,413

[22] Filed: Dec. 29, 1993

[51] Int. Cl.$^6$ .............. A61K 38/51; C12Q 1/68; C12N 9/88
[52] U.S. Cl. .......... 424/94.5; 424/94.3; 435/4; 435/6; 435/7.4; 435/232; 514/46
[58] Field of Search ................. 424/94.5, 94.3; 435/4, 6, 7.4, 232; 514/46

[56] References Cited

U.S. PATENT DOCUMENTS

| | | | |
|---|---|---|---|
| 4,179,337 | 12/1979 | Davis et al. | 435/181 |
| 5,122,614 | 6/1992 | Zalipsky | 548/520 |

OTHER PUBLICATIONS

S. Ito et al. J. Biochem. 79:1263–1272 (1976).
M. J. Tisdale, Biochemical. Pharmacology 32(19) 2915–2920 (1983).
D. Ragione et al. Biochem. J. 281:533–535 (1992).
T. Nobori et al. Cancer Res. 51(12) 3193–3197 (Dec. 1991).
T. Nobori et al. Cancer Res. 53:1098–1102 (Mar. 1993).
J. S. Schwamburn et al. Ann. Hematology 65(Suppl.) A121 (Oct. 1992).
V. K. Lishko et al. Anticancer Res. 13:1465–1468 (1993).
W. Kreis et al. Cancer. Res. 40:634–641 (Mar. 1980).
T. Nakayama et al. Biochemistry 27:1587–1591 (1988).
Specific Labeling of the Essential Cysteine Residue of Lmethionine γ–Lyase with a Cofactor Analogue, N–(Bromoacetyl) pyridoxamine Phosphate Nakayama, et al., Biochemistry, 27:1587–1591, 1988.
Deficiency of 5-deoxy-5-methylthioadenosine phosphorylase activity in malignancy Ragione, et al., Biochem. J., 281:533–538, 1992.
Methylthioadenosine Phosphorylase Deficiency in Human Leukemias and Solid Tumors Fitchen, et al., Cancer Research, 46:5409–5412, Oct. 1986.
Selective killing of human malignant cell lines deficient in methylthioadenosine phosphorylase, a purine metabolic enzyme Kamatani, et al., Proc. Natl. Acad. Sci. USA, No. 2, 78:1219–1223, Feb. 1981.

Methionine Dependency of Malignant Tumors Willi Kreis, et al., J. Natl. Cancer Inst., No. 83, 10:725, 1991.
Absence of Methythioadenosine Phosphorylase in Human Gliomas Nobori, et al., Cancer Research, 51:3193–3197, Jun. 15, 1991.
Purification and Characterization of methionine γ–lyase from Trichomonas vaginalis Lockwood and Coombs, Biochem. J., 279:675–682, 1991.
Methylthioadenosine Phosphorylase Deficiency in Human Non–Small Cell Lung Cancers Nobori, et al., Cancer Research, 53:1098–1101, Mar. 1, 1993.
A phase II trial of peg-L-asparaginase in the treatment of non–hodgkins lymphoma Muss, et al., Invest. New Drugs, 8:125–130, 1990.
Tumor Therapy by Deprivation of L–Methionine: Rationale and Results Willi Kreis. Cancer Treatment Rpt. No. 6, 63:1069–1072, 1979.
A Methionine Salvage Pathway Robert H. Abeles, Aldrichimica acta, No. 1, 25:3–7, 1992.
Biological Effects of Enzymatic Deprivation of Lmethionine in Cell Culture and an Experimental Tumor Kries and Hession, Cancer Research, 33:1866–1869, Aug. 1973.
Microtiter format gene quantification by covalent capture of competitive PCR products: application to HIV-1 detection Kohsaka, et al., Nucleic Acids Research, No. 15, 21:3469–3472, Jun. 7, 1993.

Primary Examiner—Robert A. Wax
Assistant Examiner—Rebecca Prouty
Attorney, Agent, or Firm—Fish & Richardson P.C.

[57] ABSTRACT

An improved method for chemotherapy of mammalian malignant cells which have an absolute requirement for methionine but lack methylthioadenosine phosphorylase (MTAse). The method comprises detection of MTAse negative cells in a mammal, administration of methionine γ-lyase in sufficient amounts to reduce the volume of MTAse negative cells in the mammal, and co-administration of methylthioadenosine in amounts sufficient to ensure the continued availability of methionine to the mammal's non-malignant cells. Means for detection of MTAse negative cells are provided. Means for production and use of recombinant chemotherapeutic agents are also provided.

10 Claims, 4 Drawing Sheets

METHOD FOR SELECTIVE METHIONINE STARVATION OF MALIGNANT CELLS IN MAMMALS

BACKGROUND OF THE INVENTION

1. Field of the Invention

This invention relates to a method for the selective destruction of malignant cells in mammals based on metabolic differences between those cells and non-malignant (i.e., "normal") cells. More specifically, it relates to starvation of malignant cells which lack the enzyme necessary to convert methylthioadenosine to methionine by degrading plasma methionine and homocysteine.

2. History of the Invention

The amino acid methionine (MET) is necessary for the growth of normal and malignant cells. In certain malignant cells this requirement is absolute, i.e., without an adequate supply of MET, the cells die.

In mammalian cells, MET is obtained from three sources. It can be obtained in the diet, or through biochemical synthesis of MET from L-homocysteine (homocysteine) or methythioadenosine (MTA) (a product of the polyamine biosynthetic pathway). In the latter case, MTA is converted to MET by methyethioadenosine phosphorylase (MTAse).

In the past decade, researchers have identified many malignant cell lines which lack MTAse and cannot, therefore, convert MTA to MET. For example, Katamari, et al., *Proc. Nat'l Acad. Sci. USA*, 78:1219–1223 (1981) reported that 23% of 3 human malignant tumor cell lines lacked detectable MTAse, while MTAse activity was present in each of 16 non-malignant cell lines studied. MTAse negative cells principally fulfill their requirement for MET through conversion of homocysteine. However, when homocysteine is not available, the cells will generally die.

L-methionine-L-deamino-y-mercaptomethane lyase (ED 4.4.1.11; METase) is known to degrade not only MET but also homocysteine. Theoretically, therefore, one could starve malignant cells which lack MTAse (i.e., MTAse negative cells) by degrading plasma MET and homocysteine with METase. Normal MTAse positive cells would be expected to fulfill their requirement for MET by the continued conversion of MTA to MET.

A rudimentary version of this approach was first proposed in 1972 by Kreis in *Cancer Treat. Rprts.*, 63:1069–1072 (1972). Using 11 malignant cell lines in MET-free cultures, Kreis was able to inhibit the growth of certain of the malignant cells by applying METase to the cultures. Kreis also observed that 2 normal cell lines were partly "rescued" from the effects of MET starvation when homocysteine was added to the cultures. However, while these in vitro studies were encouraging, several obstacles were described by Kreis as being in the way of a successful in vivo use of METase in chemotherapy, including the unavailability of means to ensure the survival of normal cells in vivo, the potential immunogenicity of purified or partially purified enzyme, and the need for the enzyme to be resistant to degradation by proteolytic enzymes in vivo (Kries, Chemotherapy (Muggia, FM, ed., The Hague, Boston, and London: Martinus-Nijihoff, 1983), pp. 219–248).

Another obstacle to the development of a successful approach to MET starvation of malignant cells has been the need to identify which malignancies are suitable targets for the therapy; i.e., which malignancies are MTAse negative. To that end, an assay was developed which predicts whether a malignancy is MTAse negative by determining whether any catalytic activity is present in a cell culture (Seidenfeld, et al., *Biochem. Biophys. Res. Commun.*, 95:1861–1866, 1980). However, because of the commercial unavailability of the radiochemical substrate required for the activity assay, its use in routine evaluations is not presently feasible. Moreover, the activity assay does not account for the catalytic lability of MTAse in vitro by detecting whether any of the enzyme is present in the cell culture regardless of whether it is catalytically active at the time that the assay is performed.

This limitation of the activity assay could be avoided by the development of an immunoassay which is sufficiently sensitive to detect relatively minute quantities of enzyme. However, the purification of the MTAse enzyme from natural sources to develop antibodies for use in immunological detection of MTAse has proven to be a laborious process which produces relatively poor yields (Raglone, et al., *J. Biol. Chem.*, 261:12324–12329, 1986).

Even if adequate means were developed to detect MTAse negative cells, production of an adequate supply of METase from natural sources has been as difficult as the production of MTAse. Production of METase by means other than purification of the native enzyme has not yet been achieved, in part because the gene for METase has (to date) been only partially sequenced (Nakayama, et al., *Biochem*, 27:1587–1591, 1988).

For all of these reasons, an effective approach to in vivo MET starvation of MTAse malignant cells has remained elusive. The present invention addresses this need.

SUMMARY OF THE INVENTION

In combination with means for detecting MTAse negative cells, the invention comprises an improved method for the selective starvation of MTAse negative cells. According to the method, a malignancy which has been determined to be MTAse negative is treated with a therapeutically effective amount of METase, preferably recombinant METase, and most preferably recombinant METase conjugated to polyethylene glycol or an equivalent molecule. More specifically, METase is administered to a mammal (preferably a human) in a dosage which will its lower plasma MET levels to an extent sufficient to starve MTAse negative cells of methionine (which will generally occur at about $\leq 10\%$ of the pre-therapy level of methionine). Normal (MTAse positive) cells are supplied with MET through the substantially contemporaneous administration of MTA.

The invention also comprises in part a method for detecting MTAse negative cells in a malignancy. More specifically, it comprises in one aspect the production of anti-MTAse antibodies (including monoclonal antibodies) and their use in an immunoassay for MTAse. In another aspect, it comprises detection of the presence of the gene which encodes MTAse by use of an assay based on nucleic acid amplification techniques, in particular the polymerase chain reaction (PCR).

The invention also comprises recombinant METase developed from the isolation and cloning of the gene encoding METase, thus enabling the production of substantial quantities of METase for use in the methods of the invention.

DETAILED DESCRIPTION OF THE INVENTION

I. METHOD FOR DETECTION OF MTAse NEGATIVE CELLS.

Figure 1:
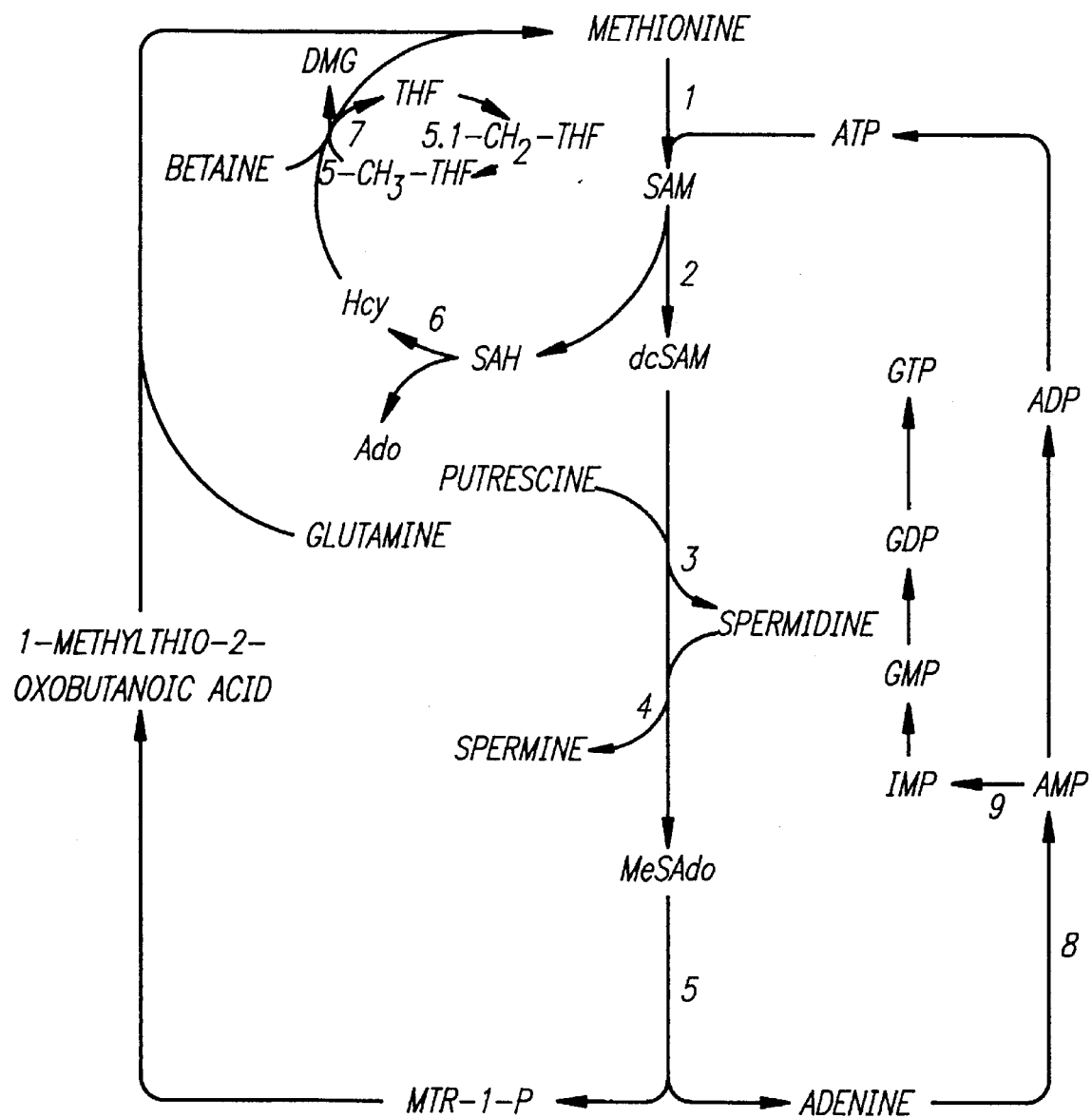
FIG. 1 is a schematic of the metabolic pathway for polyamine synthesis and reduction of MTA by MTAse.

FIG. 1 schematically depicts the metabolic pathways for in vivo synthesis of MET from MTA and degradation of MET by METase. As indicated above, to gain the full benefits of a methionine starvation cancer therapy, MTAse negative cells must be detected in the target malignancy. To that end, alternative means of detecting MTAse which are suitable for use in the methods of the invention are described below.

A. Immunoassay for MTAse.

1. Production of Antigenic MTAse and MTAse Peptides.

Antibodies which are specific for MTAse are produced by immunization of a non-human with antigenic MTAse or MTAse peptides. Generally, the antigenic MTAse peptides may be isolated and purified from mammalian tissue according to the method described by Ragnione, et al., *J. Biol. Chem.*, 265: 6241–6246 (1990). An example illustrating the practice of this method is provided in the Examples below. For reference, the amino acid sequence for full-length MTA is included herein as SEQ. ID. NO. 1.

2. Immunization with Antigenic MTAse Peptides to Produce Anti-MTAse Antibodies

Once antigenic MTAse or MTAse peptides are obtained, antibodies to the immunizing peptide are produced by introducing peptide into a mammal (such as a rabbit, mouse or rat). For purposes of illustration, the amino acid sequences of two antigenic MTA peptides are provided in the Sequence Listing appended hereto as SEQ ID. Nos. 2 and 3. Antibodies produced by rabbits immunized with these peptides showed a 50% maximal response to purified MTA at, respectively, a 1:1500 and a 1:4000 dilution.

A multiple injection immunization protocol is preferred for use in immunizing animals with the antigenic MTAse peptides (see, e.g., Langone, et al., eds., "Production of Antisera with Small Doses of Immunogen: Multiple Intradermal Injections", *Methods of Enzymology* (Acad. Press, 1981)). For example, a good antibody response can be obtained in rabbits by intradermal injection of 1 mg of the antigenic MTAse peptide emulsified in Complete Freund's Adjuvant followed several weeks later by one or more boosts of the same antigen in Incomplete Freund's Adjuvant.

If desired, the immunizing peptide may be coupled to a carrier protein by conjugation using techniques which are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit). Because MTAse is presently believed to be conserved among mammalian species, use of a carrier protein to enhance the immunogenecity of MTAse proteins is preferred.

Polyclonal antibodies produced by the immunized animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies (see, for example, Coligan, et al., Unit 9, *Current Protocols in Immunology*, Wiley Interscience, 1991).

For their specificity and ease of production, monoclonal antibodies are preferred for use in detecting MTAse negative cells. For preparation of monoclonal antibodies, immunization of a mouse or rat is preferred. The term "antibody" as used in this invention is meant also to include intact molecules as well as fragments thereof, such as for example, Fab and F(ab')$_2$, which are capable of binding the epitopic determinant. Also, in this context, the term "mAb's of the invention" refers to monoclonal antibodies with specificity for MTAse.

The general method used for production of hybridomas secreting monoclonal antibodies ("mAb's") is well known (Kohler and Milstein, *Nature*, 256:495, 1975). Briefly, as described by Kohler and Milstein, the technique comprised isolation of lymphocytes from regional draining lymph nodes of five separate cancer patients with either melanoma, teratocarcinoma or cancer of the cervix, glioma or lung. The lymphocytes were obtained from surgical specimens, pooled, and then fused with SHFP-1. Hybridomas were screened for production of antibody which bound to cancer cell lines. An equivalent technique can be used to produce and identify mAb's with specificity for MTAse.

Confirmation of MTAse specificity among mAbs of the invention can be accomplished using relatively routine screening techniques (such as the enzyme-linked immunosorbent assay, or "ELISA") to determine the elementary reaction pattern of the mAb of interest.

It is also possible to evaluate an mAb to determine whether it has the same specificity as a mAb of the invention without undue experimentation by determining whether the mAb being tested prevents a mAb of the invention from binding to MTAse. If the mAb being tested competes with the mAb of the invention, as shown by a decrease in binding by the mAb of the invention, then it is likely that the two monoclonal antibodies bind to the same or a closely related epitope.

Still another way to determine whether a mAb has the specificity of a mAb of the invention is to pre-incubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention.

3. Immunoassay Protocol for Detection of MTAse Negative Cells.

Once suitable antibodies are obtained as described above, they are used to detect MTAse in a malignancy. An example of an immunoassay suitable for this purpose (i.e., an immunoblot method) is described further in Example I below. However, those skilled in the immunological arts will recognize that MTAse may be detected using the antibodies described above in other immunoassay formats, in either liquid or solid phase (when bound to a carrier).

Detection of MTAse using anti-MTAse antibodies can be done utilizing immunoassays which are run in either the forward, reverse, or simultaneous modes, including immunohistochemical assays on physiological samples. Suitable immunoassay protocols include competitive and non-competitive protocols performed in either a direct or indirect format. Examples of such immunoassays are the radioimmunoassay (RIA) and the sandwich (immunometric) assay. Those of skill in the art will know, or can readily discern, other immunoassay formats without undue experimentation.

In addition, the antibodies utilized in the immunoassays may be detectably labelled. A label is a substance which can be covalently attached to or firmly associated with a nucleic acid probe which will result in the ability to detect the probe. For example, a level may be radioisotope, an enzyme substrate or inhibitor, an enzyme, a radiopaque substance (including colloidal metals), a fluoresceors, a chemiluminescent molecule, liposomes containing any of the above labels, or a specific binding pair member. A suitable label will not lose the quality responsible for detectability during amplification.

Those skilled in the diagnostic art will be familiar with suitable detectable labels for use in in vitro detection assays. For example, suitable radioisotopes include $^3H$, $^{125}I$, $^{131}I$, $^{32}$, $^{14}C$, $^{35}S$. Amplified fragments labeled by means of a radioisotope may be detected directly by gamma counter or by densitometry of autoradiographs, by Southern blotting of the amplified fragments combined with densitometry. Examples of suitable chemiluminescent molecules are acridines or luminol. Target Sequences hybridized with probes derivatized with acridium ester are protected from hydrolysis by intercalation. Examples of suitable fluorescers are fluorescein, phycobiliprotein, rare earth chelates, dansyl or rhodamine.

Examples of suitable enzyme substrates or inhibitors are compounds which will specifically bind to horseradish peroxidase, glucose oxidase, glucose-6-phosphate dehydrogenase, β-galactosidase, pyruvate kinase or alkaline phosphatase acetylcholinesterase. Examples of radiopaque substance are colloidal gold or magnetic particles.

A specific binding pair comprises two different molecules, wherein one of the molecules has an area on its surface or in a cavity which specifically binds to a particular spatial and polar organization of another molecule. The members of the specific binding pair are often referred to as a ligand and receptor or ligand and anti-ligand. For example, if the receptor is an antibody the ligand is the corresponding antigen. Other specific binding pairs include hormone-receptor pairs, enzyme substrate pairs, biotin-avidin pairs and glycoprotein-receptor pairs. Included are fragments and portions of specific binding pairs which retain binding specificity, such as fragments of immunoglobulines, including Fab fragments and the like. The antibodies can be either monoclonal or polyclonal. If a member of a specific binding pair is used as a label, the preferred separation procedure will involve affinity chromatography.

The antibodies may also be bound to a carrier. Examples of well-known carriers include glass, polystyrene, polypropylene, polyethylene, dextran, nylon, amyloses, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

B. Detection of MTAse Negative Cells Using a PCR-based Assay.

For the relative ease and speed of detection provided by immunoassay using the MTAse-specific antibodies described herein, the immunoassay is the preferred means for detection of MTAse-negative cells. However, those skilled in the art will also recognize that other detection means to detect the presence of MTAse negative cells in a malignancy may be used. For example, using the nucleic acid sequence description in SEQ ID NO 1, one of skill in the art could construct oligonucleotide probes which would hybridize to MTAse DNA present in a cell sample. Conversely, because it is believed that MTAse deficiency results from the genomic deletion of the gene which would encode the MTAse protein, it can be assumed that if no gene encoding MTAse is detected in a cell sample that the cells are MTAse negative.

A detailed description of a protocol for the amplification and detection of the MTAse gene is provided in co-pending U.S. patent application Ser. No. 08/176,855, filed Dec. 9, 1993. The disclosure of co-pending application Ser. No. 08/176,855 pertaining to this protocol is incorporated herein by this reference.

C. MTAse Negative Candidates for MTAse Starvation Therapy

A malignancy which is a candidate for the therapy of the invention (i.e., MET starvation therapy) is one in which the MTAse protein, whether catalytically active or catalytically inactive, is not detectably present. In all malignant cell lines studied to date, MTAse negativity (if present) is a consistent trait throughout the cell population. In other words, if some cells of a malignancy are MTAse negative, it can be expected that all cells of the malignancy will be MTAse negative. This is consistent with the present belief in the art that MTAse deficiency is the result of a gene deletion rather than a mutation. The homogeneity of a malignancy for MTAse negativity should significantly enhance the efficacy of MET starvation as a cancer therapy in comparison to therapies directed to heterogeneous traits, such as tumor antigens targeted in monoclonal antibody therapy. However, it is sufficient for purposes of the invention that the malignancy be "substantially deficient" in MTAse; i.e., that they contain no detectable quantities of MTAse protein.

Human malignancies which are presently believed to be substantially deficient in MTAse include:

TABLE 1

| Malicinancy | MTAse deficiency determined by: |
|---|---|
| Non-small cell lung cancers: | Immunoassay♦ |
| A-549 (Adenosarcoma) | |
| Sk-Lu-1 (Adenosarcoma) | |
| H322 (bronchoalvedor) | |
| H1334 (large cell carcinoma) | |
| H1437 (adenosarcoma) | |
| H1581 (large cell carcinoma) | |
| *Brain tumor cell lines: | Immunoassay♦ |
| A172 | |
| U-87MG | |
| U-1 38MG | |
| Hs683 | |
| Primary brain tumors: | Immunoassay♦ |
| Astrocytoma | |
| Glioblastoma multiforme | |
| Oligostrocytoma | |
| Lymphomas and leukemias: | Immunoassay♦ |
| CEM (acute lymphocytic leukemia) | |
| K-T-1 (acute lymphocytic leukemia) | |
| NALL-1 (acute lymphocytic leukemia) | |
| K562 (chronic myelogenous leukemia) | |
| DHL-9 (malignant lymphoma) | |
| HSB2 (acute lymphocytic leukemia) | |
| Other: | |
| Walker 256 sarcinosarcoma | Clinical evidence** |
| Jurkat | Immunoassay*** |

TABLE 1-continued

| Malicinancy | MTAse deficiency determined by: |
|---|---|
| K562 | Immunoassy*** |
| Capan-1 (adenosarcoma of pancreas) | Immunoassay**** |

LEGEND:
*obtained from the American Type Culture Collection, Rockville, MD.
**reported by Kries, et al., Cancer Res., 33:1866–1869 (1973)
***reported by Rangione, et al., Biochem. J. 281:533–538 (1992)
****reported by Kries, et al., Cancer Trmt. Rpts., 63:1069–1072 (1979)
♦MTAse deficiency in all other malignancies was detected and reported by Nobori, et al., in Cancer Res. 53:1098–1101 (1993) and in Cancer Res. 51:3193-3197 (1991).

Using the detection techniques described herein, those skilled in the art will be able to detect MTAse deficiency in other malignancies without undue experimentation.

II. MET STARVATION THERAPY

A. Production of METase

For use in the methods of the invention, sources of both MTA and METase are required. Means for obtaining MTA are described supra. For use in the methods of the invention, METase has been purified from microorganisms including *Trichomonas vaginalis* (Lockwood, et al., *J. Biochem.* 279:675–682, 1991), *Clostridium sporogenes* (see, e.g., Kries, et al., supra at 1867; EC4.4.1.11), and *Pseudomonas putida* (Nakayama, et al., *Biochem.*, 27:1587–1591, 1988).

Using a cDNA library constructed from *P. putida*, the full-length nucleotide sequence for METase has been identified and is contained in the Sequence Listing appended hereto as SEQ. ID. No. 4; the amino acid sequence is contained in SEQ ID NO. 5.

With this information, METase can be readily synthesized or expressed from a DNA clone using well-known techniques as described above with respect to MTAse. A detailed example of how METase can be cloned and expressed in *E. coil* is provided further below in Examples II and III.

While purified, partially purified, synthesized or recombinant METase may be used in the therapeutic method of the invention, the latter is preferred for its ease of production and relatively low immunogenicity. The immunogenicity of the enzyme can be, and preferably will be, further reduced by coupling it to polyethylene glycol (PEG) or an equivalent, biologically compatible molecule. Coupling to PEG can also be expected to increase the half-life of the METase conjugate in vivo.

The PEG-METase conjugate can be formed by covalent attachment of PEG to the enzyme as described with respect to L-asparagine (see, e.g., Benedich, et al., *Clin. Exp. Immunoi.* 48:273–278, 1982). Methods for coupling PEG to proteins are well-known in the art and will not, therefore, be described further in detail here. Based on results observed in human clinical trials for treatment of non-hodgkins lymphoma with L-asparaginase coupled to PEG, coupling of METase to PEG would not be expected to significantly reduce its activity in vivo (see, re in vivo results obtained with PEG-L-asparaginase, Muss, et al., *Invest. New Drugs*, 8:125–130 (1990)). Those skilled in the art will recognize, however, that other means for extending the half-life of proteins in vivo are known and may be suitable for use with METase including, but not limited to, glycosylation and succinylation.

B. Therapeutic Methods. Malignancies which are substantially deficient in MTAse will be treated according to the invention in part by administration of METase. Preferably, these malignancies will be those which can be treated by regional chemotherapy; i.e., where the malignancy is localized and contained in an area of the body which is accessible by intra-arterial infusion or by introduction through topical, transdermal or equivalent routes for administration of the METase directly to the locus of the malignancy. Examples of malignancies which are susceptible to regional chemotherapy are melanomas, ovarian cancer (via a peritoneal catheter) and bladder cancer (via a urethral catheter). Other malignancies which, if MTAse negative, may be treated by regional chemotherapy according to the invention will be known by those skilled in oncology.

It will be appreciated by those skilled in the art that the therapeutic compositions of the invention may also be administered systemically. However, the dosages would have to be adjusted to compensate for clearance of the compositions and potential toxicity to normal cells. In particular, clinical evidence of methionine starvation of normal cells would have to be monitored closely and compensated for, if necessary, by administration of additional quantities of MTA.

Malignancies which are substantially deficient in MTAse will preferably be treated according to the invention as follows.

METase will be administered to a mammal (preferably a human) parenterally, with the preferred route of administration being intra-arterial infusion. The METase will be administered in a pharmaceutically acceptable carrier, which may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. As noted above, the METase will preferably be conjugated to PEG to reduce its immunogenicity.

Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Dosages of the METase can vary from about 10 units/m$^2$ to 20,000 units/m$^2$, preferably from about 5000 to 6000 units/m$^2$, (or lower when administered by intra-arterial infusion) in one or more dose administrations weekly, for one or several days. METase can generally be expected to be cleared by the mammal in about 24 hours after its administration; with use of means to extend the half-life of the enzyme such as PEG conjugation, this half-life may be extended by several hours to several days. The mammal's plasma methionine levels should, therefore, be monitored and additional doses of METase administered as necessary to achieve a therapeutically significant reduction of the mammal's plasma methionine concentration. This will be a reduction sufficient to induce a detectable decrease in the volume of MTAse negative cells; i.e., a decrease in the volume of malignant cells or tumor load in the mammal. A dosage which achieves this result will be considered a "therapeutically effective" dosage. Based on in vivo studies in rodents using partially purified METase, a therapeutically effective dosage can be generally expected to be one which reduces the plasma methionine level in the patient to about $\leq 10\%$ of its pre-therapy level.

Plasma methionine levels (and changes therein) can be monitored by periodic (and preferably daily) in vitro assays of blood samples drawn from the patient receiving the METase throughout the course of its administration. Generally, based on the studies done in rodents, it can be expected that plasma methionine levels will be lowered to ≦10% of their pretherapy levels within about an hour of the administration of METase. Assays for plasma methionine are well-known in the art; for example, the concentration of methionine in a blood sample can be determined using the method for gas-liquid chromatography of esterified amino acids (n-butyl ester) is described in Roach, et al., *J. Chromotog.* 44:269–278 (1969). Other equivalent procedures to detect methionine in plasma will be known to or easily identified by those of ordinary skill in the art.

It should be noted that METase cannot degrade intracellular methionine. Therefore, with an adequate supply of MTA for the formation of intracellular methionine, MTAse-positive cells will generally be able to survive the reduction of exogenous methionine by METase. However, without a supply of exogenous methionine (or the L-homocysteine substrate for methionine which is also degraded by METase), MTAse-negative cells with an absolute requirement for methionine will generally not survive the loss of plasma methionine.

The efficacy of the therapy may be confirmed and monitored by any clinical evidence indicative of a reduction in the cellular volume of the malignancy (determined by means well known in the art) and/or periodic detection of the MTAse-negative cell volume in the malignancy using the detection means described herein. Based on clinical data regarding the use of L-asparaginase therapy in humans, it can be expected that the toxicity of the METase therapy will be fairly low and may consist primarily of allergic reactions treatable by means well known to those skilled in the clinical art, such as administration of epinephrine.

Therefore, MTA will be administered to the mammal substantially concurrently with METase. Preferably, the MTA and METase will be administered at the same time. Because MTA will not act as a substrate for METase, the two may be combined together in a pharmaceutically acceptable carrier. Alternatively, the MTA may be administered within about 24 hours of the administration of the METase (and preferably sooner) to "rescue" the MTAse positive cells whose endogenous supply of methionine is becoming exhausted.

The dose of MTA needed to rescue normal cells will vary depending on a number of clinical factors, including the location of the malignancy, the volume of MTAse negative cells in the malignancy, the length of METase therapy and the availability to the patient of dietary MET. Generally, however, the MTA will be administered in dosages sufficient to maintain a plasma methionine level of about 1–10 μM.

The invention having been fully described, examples illustrating its practice are set forth below. These examples should not, however, be considered to limit the scope of the invention, which is defined by the appended claims.

In the examples, the abbreviation "min." refers to minutes, "hrs" and "h" refer to hours, and measurement units (such as "ml") are referred to by standard abbreviations.

EXAMPLE I

IMMUNOASSAY FOR MTAse

A. Production of MTAse Antibodies

MTAse was purified from bovine liver as described by Ranglone, et al, supra. Several tryptic peptides from the isolated enzyme were sequenced using conventional techniques. Based upon the sequences obtained, peptides 40 (18 amino acids long; see SEQ. I.D. No. 2) and 51 (14 amino acids long; see SEQ. I.D. No. 3) were synthesized by a modification of the well-known Merrifield solid-phase method (see, e.g., Chen, et al., *Proc. Nat'l Acad. Sci. USA*, 81:1784–1788, 1984). All peptides contained a cysteine residue at the carboxy terminus to facilitate chemical coupling to the carrier protein, KLH, with m-maleimidobenzoyl-N-hydroxysuccimide ester.

New Zealand white rabbits (two rabbits per peptide) were immunized n a bimonthly basis with the peptide-KLH conjugates. The initial injections contained 1 mg of synthetic peptide-KLH conjugate emulsified in Freund's complete adjuvant. Booster injections had 1 mg of antigen in incomplete Freund's adjuvant. After 3–4 injections, sera were partially purified with 50% saturated ammonium sulfate and were screened for anti-peptide and anti-MTAse reactivities by ELISA.

More specifically, microtiter plates were precoated with peptides or MTAse at 10 μg/ml in BBS (0.2M sodium borate-0.15M NaCl, pH 8.5) overnight at 4° C. The plates were washed once in BBS containing 0.05% Tween 20 and then were incubated for 4 hours with BBS containing 1% bovine serum albumin to block nonspecific binding sites. Several dilutions of a control serum or peptide-induced antisera were then applied in 0.1-ml aliquots and incubated overnight. The plates were washed twice with BBS containing 0.05% Tween 20, and then exposed for 1 hour to alkaline phosphatase-labeled goat F(ab')$_2$anti-rabbit immunoglobulin (Jackson Laboratories, Inc., West Grove, Pa.) at a dilution of 1:1000 in BBS. After the plates were washed, 0.2 ml of −0.1M p-nitrophenyl phosphate disodium in 0.1M NaHCO$_3$, pH 9.0, was added to each well. The absorption at 405 nm was measured 30 minutes later.

B. Protocol for Immunoblot Analysis for Immunoreactive MTAse

Several human cell lines and tumor biopsies were evaluated for the presence of MTAse-negative cells (see, re the MTAse-negative cells, Table I, items marked "immunoassay"). Other sample which tested MTAse-positive were BV-173 (a chronic myelogenous leukemia, "CML"), Molt-16 (an acute lymphoctic leukemia, "ALL"), Molt-4 (ALL), U397 (histiocytic lymphoma), SUP-T8 (ALL), U-373MG (glioblastoma), and T98G (glioblastoma).

Cell extracts prepared from enzyme-positive cells were electrophoresed on a 12.5% polyacrylamide gel containing 0.1% sodium dodecyl sulfate along with various amounts of MTAse which was purified from bovine liver as described above.

More particularly, the crude cell extracts (10–150 μg/lane) were separated by electrophoresis in 12.5% polyacrylamide gels containing 0.1% sodium dodecyl sulfate. After electrotransfer to nitrocellulose membranes (0.45 mm; Bio-Rad, Richmond, Calif.), nonspecific binding sites were blocked with 3% powdered milk in BBS. The proteins were then probed for 16 h at room temperature with antisera diluted 1:500 in BBS containing 3% powdered milk. After the proteins were washed extensively with BBS, reactive bands were detected by the binding of $^{125}$I-protein A (ICN Radiochemicals, Irvine, Calif.) for 1 hour. The membranes were washed and blotted onto paper towels and exposed to Kodak XAR-5 (tm) film at −70° C.

The bands on the autoradiographs were scanned with a densitometer (Bio-Rad) and were quantitated using a calibration curve obtained from the immunoreactive bands of the purified enzyme.

C. Results

Figures 2A, 2B:
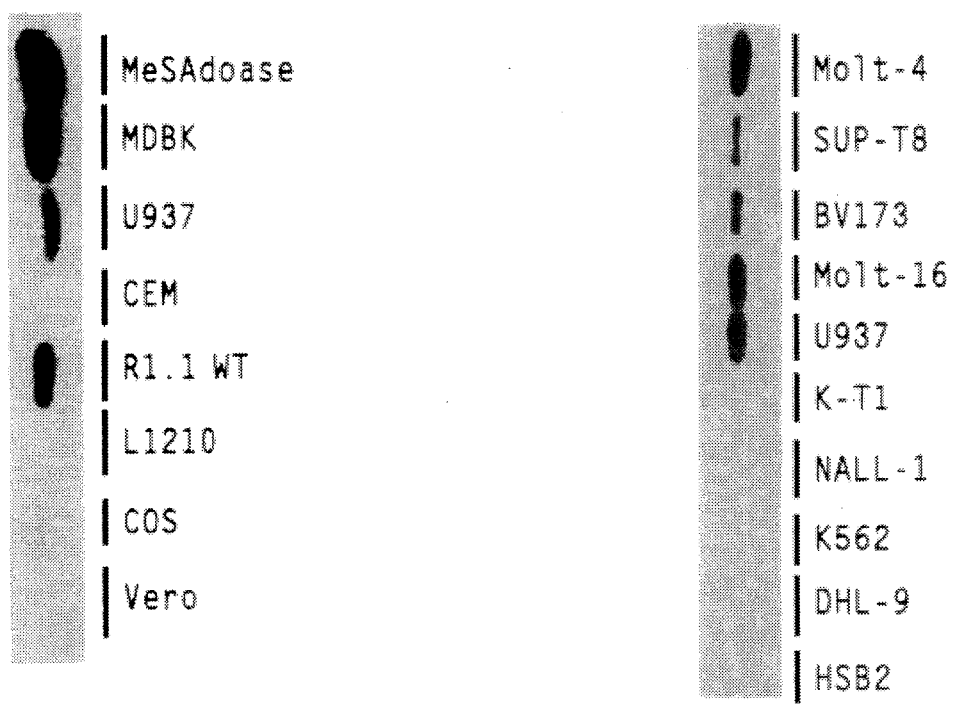
FIGS. 2A and B are a comparison of MTAse positive and MTAse negative human and non-human cell lines detected by immunoblot analysis.
Figure 3B:
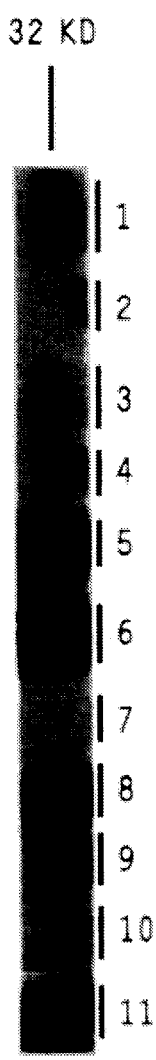
FIGS. 3A and B are a comparison of MTAse positive and MTAse negative human cell lines and primary tumors detected by immunoblot analysis.
Figure 3A:
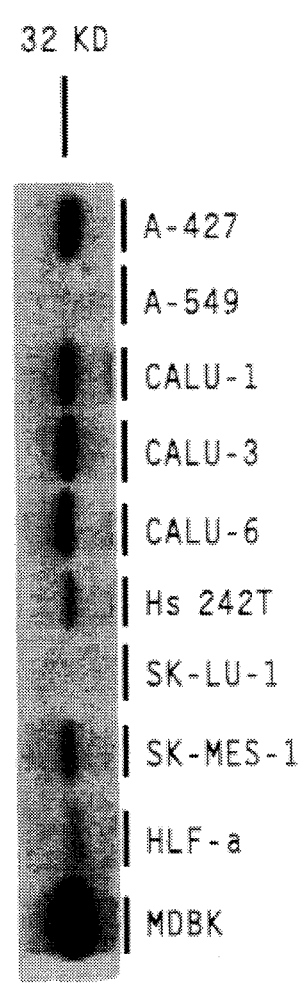

In the non-lung cell lines and biopsies (i.e., in the gliomas), sixty-seven percent (4 of 6) were entirely deficient in immunoreactive enzyme (FIG. 2). Six successive biopsy specimens from human gliomas, with different histological characteristics (Table I), five were entirely deficient (FIG. 3). Control experiments showed that normal human brain has abundant MTAse activity (FIG. 3, lane 7). Thus, complete MTAse deficiency is a common and specific metabolic abnormality in human gliomas.

Figure 4:
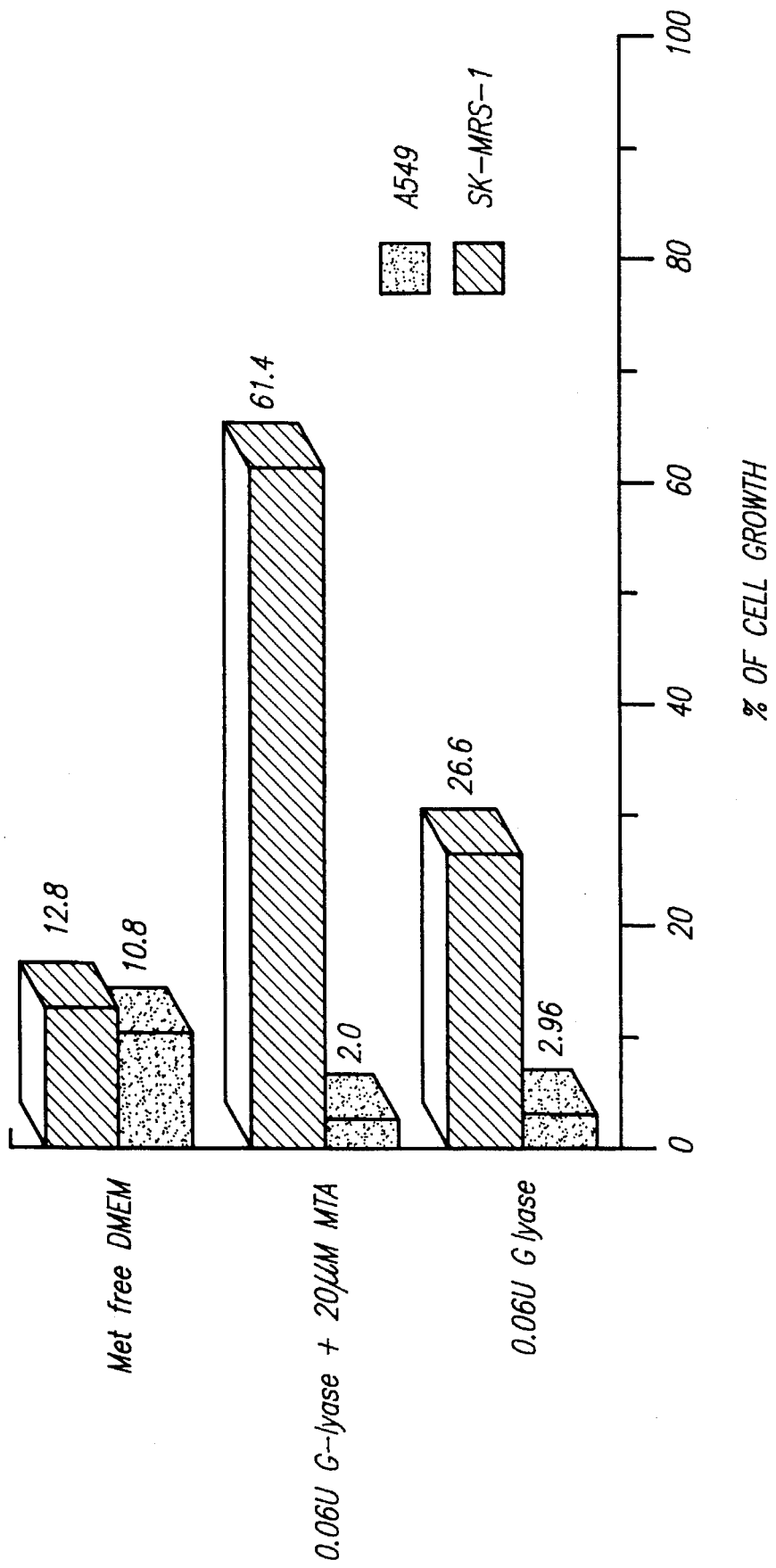
FIG. 4 is a comparison of the growth experienced by MTAse negative human cells treated with METase versus those grown in a methionine rich environment.

Of 19 non-small cell lung cancer cell lines tested, MTAse was entirely lacking in 6 cell lines (see, Table I and FIG. 4).

EXAMPLE II

CLONING OF METase FROM Psuedomonas putida

Referring to the partial amino acid sequence for METase published by Wakayama, et al., *Biochem*, 27:1587–1591, 1988), degenerate oligonucleotide primers were designed and used in a PCR assay for the gene for METase.

This PCR assay amplified a fragment of approximately 300 bp. The 300 bp PCR product was subcloned into the plasmid pBluescript II KS (Stratagene, San Diego). Using an internal oligonucleotide probe to the PCR product, Southern blot analysis of this subcloned PCR product verified the identity of this fragment to be of the METase gene. Further Southern blot analysis showed that this PCR generated fragment hybridized to a 5.0 kb Bgl II fragment in *Pseudomonas putida* DNA.

Based on these results, a bacteriophage genomic DNA library was constructed containing *Psuedomonas putida* genomic DNA. Bgl II digested *Psuedomonas putida* was electrophoresed on a 0.8% low melting point agarose gel. Bgl II fragments ranging in size of 4/kb to 6/kb were excised and purified from the gel. Using Klenow fragment, these Bgl II fragments were partially filled-in and subcloned into the bacteriophage vector, γFix II. This vector was digested with Xho I and partially filled-in-with Klenow. The library was packaged into bacteriophage particles using gigapack packaging extract from Stratagene. After packaging, the library was amplified and titered.

To isolate the complete METase gene, this library was screened using the PCR generated fragment. After screening 200,000 clones, eight independent primary clones were isolated. From these eight clones, only two clones were truly positive and unique. One clone contained a 5.1 kb insert and the other contained a 5.9 kb insert. These inserts were subcloned into pBluescript II KS and were subsequently mapped and sequenced. We determined that the sequence for the METase gene was 1 61 5 bp (See, SEQ.ID.No. 4).

EXAMPLE III

EXPRESSION OF RECOMBINANT METase

The recombinant METase gene was expressed in the C5 vector. This is the same vector used for the expression of MTAse (see, e.g., co-pending U.S. application Ser. No. 08/176,855, filed Dec. 29, 1993. A single colony of C5 recombinant cloned *E. coli* was used to inoculate a 50 ml of culture. Standard LB medium was used supplemented with 50 μg/ml ampicillin for both and large scale bacterial cultures. Inoculated 50 ml culture was incubated at 37° C. overnight. The overnight culture was diluted 100-fold into fresh LB medium. Cells were grown in large culture (1l) for 1.5 hours with rigorous shaking at 37° C. To induce the METase expression, isopropylthio-β-D-galactoside [IPTG] was added at a final concentration of 0.01, 0.1, and 1 mM to the large culture and the cultures were incubated for an additional 4 hours. The optimum IPTG concentration for protein expression was found to be 1 mM.

Four hours following IPTG addition, the cells were collected and harvested by centrifugation at 19.000×g 10 min. at 4° C. Supernatant was removed and pellet was suspended and washed in cold saline, then centrifuged again. The resuspended cell pellet was washed in 100–200 ml of 20 mM potassium phosphate buffer, pH 7.5, containing 15 μM 2-mercaptoethanol. One mM-EDTA and 30 μM-pyridoxal 5'-phosphate (buffer A) was added, then the pellet was spun again. The washed resuspended (in buffer) cell suspension was placed into cell disruption bomb. Cell breakage was done using 2.200 PSI $N_2$ pressure for 20 minutes. The lysed cells were centrifuged 43.000×g for 20 min. at 4° C. The supernatant from the cell extract was further purified with dye-ligand affinity column.

Cell extract (10 ml) was placed onto a "DYEMATRIX" gel [Orange A] (Amicon Inc., Beverly, Mass.) column (12×2.6 cm). The column was packed and equilibrated following the manufacturer's instructions. After the sample loading the column was flushed with 5 column volumes of buffer A to remove unbound material. After this step, bound product was eluted with a 0–1.5M KCl linear gradient in buffer A. Ten ml fractions were collected and subjected to the γ-lyase enzyme assay. The fractions containing the major peak of methionine γ-lyase activity were pooled and concentrated to 2–3 ml by "CENTRICON 30" (Amicon Inc.).

Solid $(NH_4)2SO_4$ was added to the concentrated fractions (0.314 g/ml) to give a final concentration of 2.4M, and the sample was centrifuged 13.000×g for 10 min. and supernatant was filtered with a 0.45μ acrodis filter (Amicon, Inc.) before injection onto an Alkyl "SUPEROSE" (agarose) Hr 5/5 hydrophobic-inter-action-FPLC column (Pharmacia), that had been equilibrated with 2.4M $(NH_4)_2SO_4$ dissolved in the buffer A used for previous steps. The bound protein was eluted by linearly decreasing the (NH4)2SO4 concentration (flow rate 0.5 ml/min.). Fractions containing METase activity were pooled and concentrated as described earlier. The protein concentration was measured by the method described by Bradford.

The purity of enzyme preparation was checked by SDS 10% glycine-tris 1 mm gel (Novex, San Diego, Calif.). METase activity was assayed by measuring 2-ketobutyric acid production, as described by Esaki & Skoda (*Meth. Enzymol.* 143:459465 (1987), the disclosure of which is incorporated herein). The final enzyme had a specific activity of 300 U/mg where 1 U=1μM product generated per minute.

EXAMPLE IV

SELECTIVE STARVATION OF MTAse NEGATIVE CELLS IN NON-SMALL LUNG CANCER CELL LINES

The MTAse negative non-small lung cancer cell lines identified in Example I were treated in vitro in a cell culture with METase and MTA according to the therapeutic method of the invention. Specifically, enzyme-positive (SK-MES-1) and negative (A-549) cell lines were cultured for 4 days in (a) methionine-containing medium supplemented with 10% dialyzed horse serum, (b) methionine-depleted medium supplemented with 10% dialyzed horse serum, and (c) methionine -depleted medium supplemented with 10% dialyzed horse serum and 16μM MeSAdo. The proliferation of both cell lines, especially of the enzyme-negative A-549 cells, was markedly retarded in medium lacking methionine (27 and 3.3% growth of control for SK-MES-1 and A-549 cells, respectively). When MTA was added to the same medium, it augmented the growth of enzyme-positive SK-MES-1 cells (77% growth of control). However, the proliferation of enzyme-negative A-549 cells was not enhanced in the presence of MTA (4.3% growth of control) (Table II).

These data indicate that the growth of the MeSAdo phosphorylase-negative cells may be blocked selectively in methionine-depleted, MeSAdo-supplemented medium.

TABLE II

| Cell Line | Enzyme Status[a] | Growth (% of control)[b] Methionine free | |
|---|---|---|---|
| | | Without MeSAdo | With MeSAdo |
| SK-MES-1 | + | 27 ± 2.6 | 77 ± 4.7 |
| A-549 | − | 3.3 ± 0.6 | 4.3 ± 1.1 |

[a]+, present; −, absent.
[b]Percentage of control growth = 100 × (cell growth in methionine-depleted medium with or without MTA)/(cell growth in methionine-containing medium).

EXAMPLE V

METHIONINE STARVATION OF HUMAN MALIGNANT CELLS WITH RECOMBINANT METase

To study the anti-proliferative effects of recombinant METase produced as described in Examples II and III, human SKoMES-1 and A-549 cells DMEM were cultured in medium, and 10% dialyzed fetal bovine serum supplemented with 0.06 U/ml recombinant METase. After three days, cell proliferation was determined. The effects of METase were expressed on a percentage of cell growth in medium lacking added enzyme.

As shown in FIG. 4, cell growth in the enzyme positive (SK-MES-1) and enzyme negative (A-549) METase supplemented medium increased, respectively, by 26.6 and 2.96%. However, if 20 p MTA was added as an alternate source of cellular methionine, cell growth was restored to 61.4% of the control value in enzyme positive cells, while growth in enzyme negative cells declined to 2.0%.

SUMMARY OF SEQUENCES

SEQ.ID.No. 1 is the amino acid sequence for full-length MTAse.

SEQ.ID.No. 2 is the amino acid sequence of an antigenic MTAse peptide.

SEQ.ID.No. 3 is the amino acid sequence of an antigenic MTAse peptide which differs in amino acid sequence from the peptide of SEQ.ID.No. 2.

SEQ.ID.No. 4 is the nucleotide sequence of a polynucleotide encoding METase.

SEQ.ID.No. 5 is the amino acid sequence of METase predicted from the nucleotide sequence of SEQ.ID.No. 4.

We claim:

1. A method for the selective methionine starvation of cells in a mammal which are suspected of being MTAse negative comprising:

determining whether the mammal has cells which lack catalytically active and catalytically inactive MTAse by assay means comprising:

(a) obtaining an assayable sample of cells from the mammal which are suspected of being MTAse negative, (b) adding oligonucleotide probes to the sample which will specifically hybridize to a nucleic acid that encodes MTAse, wherein the probes are added under conditions which will allow the probes to detectably hybridize to any such nucleic acid present in the sample, and (c) determining whether the nucleic acid is present in the sample, wherein the absence of nucleic acid indicates that the cells are MTAse negative;

wherein further a therapeutically effective amount of METase is administered to a mammal having MTAse negative cells and, at substantially the same time, a therapeutically effective amount of MTA is administered to the mammal.

2. The method according to claim 1 wherein the sample is further subjected to conditions which will favor the selective amplification of any MTAse encoding nucleic acid present in the sample.

3. The method according to claim 1 further comprising the step of determining the mammal's plasma methionine level prior to and after administration to the mammal of the METase.

4. The method according to claim 3 wherein the therapeutically effective amount of METase is between 10 units/$m^2$ and 20,000 units/$m^2$ administered at least once in a total amount sufficient to reduce the number of MTAse negative cells detected in the mammal.

5. The method according to claim 4 wherein the therapeutically effective amount of METase is that amount which will reduce the mammal's plasma methionine levels to about $\leq 10\%$ of its level prior to administration of the METase.

6. The method according to claim 1 wherein the therapeutically effective amount of MTA is that amount which will be sufficient to maintain a plasma MTA concentration in the mammal of about 1–10 μM.

7. The method according to claim 1 wherein the METase is a microbial protein which will specifically degrade mammalian methionine in vivo.

8. The method according to claim 7 wherein the amino acid sequence of the microbial METase is set forth in SEQ ID No. 5.

9. The method according to claim 7 wherein the METase is encoded by a polynucleotide having a nucleotide sequence as set forth in SEQ ID No. 4.

10. The method according to claim 1 wherein the METase is coupled to polyethylene glycol.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 2763 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: methyladenosine phosphatase ( i x ) FEATURE:
( A ) NAME/KEY: CDS
( B ) LOCATION: 1..2763

( x i ) SEQUENCE DESCRIPTION: SEQ ID NO:1:

```
TTTATACAGA  GCATGACAGT  GGGGTCCTCA  CTAGGGTCTG  TCTGCCACTC  TACATATTTG    60

AAACAGGAGT  GGCTTCTCAG  AATCCAGTGA  ACCTAAATTT  TAGTTTTAGT  TGCTCACTGG   120

ACTGGGTTCT  AGGAGACCCC  CTGTGTTAGT  CTGTGGTCAT  TGCTAGSAGA  ATCACTTAAT   180

TTTTTCTAGA  CTCTAGGAGA  AAACAGTTGG  TGGTGTACTC  ATCACGGGTT  AACAATTTCT   240

TCTCTCCTTC  CATAGGCATG  GAAGGCAGCA  CACCATCATG  CCTTCAAAGG  TCAACTACCA   300

GGCGAACATC  TGGGCTTTGA  AGGAAGAGGG  CTGTACACAT  GTCATAGTGA  CCACAGCTTG   360

TGGCTCCTTG  AGGGAGGAGA  TTCAGCCCGG  CGATATTGTC  ATTATTGATC  AGTTCATTGA   420

CANNNNNNNN  NNNNNNNNNN  GAGGTCGACG  GTATCGATAA  GCTTTGTAAA  CAATTGTCTT   480

TAGCTTATCC  AGAGGAATTG  AGTCTGGAGT  AAAGACCCAA  ATATTGACCT  AGATAAAGTT   540

GACTCACCAG  CCCTCGGAGG  ATGGAAAGAT  GGCCTTAAAA  TAAACAAAC   AAAAACCTTT   600
```

| | | | | | |
|---|---|---|---|---|---|
| TTTGCTTTAT | TTTGTAGGAC | CACTATGAGA | CCTCAGTCCT | TCTATGATGG | AAGTCATTCT | 660
| TGTGCCAGAG | GAGTGTGCCA | TATTCCAATG | GCTGAGCCGT | TTTGCCCCAA | AACGAGAGAG | 720
| GTGTGTAGTC | TTTCTGGAAG | GTGTACCAGA | ATAAATCATG | TGGGCTTGGG | GTGGCATCTG | 780
| GCATTTGGTT | AATTGGCAGA | CGGAGTGGCC | CCATACCCTC | ACTCAAGTTT | GCTTTGTATT | 840
| ATGCAAGTTT | ATGGAGAGTT | ATTTCCTGTT | GCTAATAATT | TNNNNNNNNN | NNNNNNNNNN | 900
| AAGTGCAGCC | TTAAGTTGTG | CATGTGCTAG | TATGTTTTGA | AGTTCTGGT | TTTTCTTTTC | 960
| TAGGTTCTTA | TAGAGACTGC | TAAGAAGCTA | GGACTCCGGT | GCCACTCAAA | GGGACAATG | 1020
| GTCACAATCG | AGGGACCTCG | TTTTAGCTCC | CGGGCAGAAA | GCTTCATGTT | CCGCACCTGG | 1080
| GGGGCGGATG | TTATCAACAT | GACCACAGTT | CCAGAGGTGG | TTCTTGCTAA | GGAGGCTGGA | 1140
| ATTTGTTACG | CAAGTATCGC | CATGGGCACA | GATTATGACT | GCTGGAAGGA | GCACGAGGAA | 1200
| GCAGTAGGTG | GAATTCTTTT | CTAAGCACAT | ATAGCATGGG | TTTCTGGGTG | CCAATAGGGT | 1260
| GTCTTAACTG | TTTGTTTCTA | TTACGTTAGT | TTCAGAAAGT | GCCTTTCTAC | AAGGTTTTGA | 1320
| AGTTGTTAAT | ATTTTCTGTA | GTTCCATTGG | AAGGTAAGAA | CAAAGATCAA | AAGAAAGAAA | 1380
| GAGACACTTT | TACCCAAGGA | TCAGTAGTGA | AAATAGTACA | TTGTAGGCAT | GTAGATGTGT | 1440
| TGAGAATCAT | ACTAAGACTT | GGGCCTTANN | NNNNNNNNNN | NNNNNNNNNN | NNTACCCTAC | 1500
| ATTGAGGATT | CGGTTTCAGC | AGATAAATTT | GAGGGACACA | AACATTTAGG | CTGTAGCAAG | 1560
| GCTGGAGCTC | AGAAAAATGT | TTTATGACAA | GCAGTGGAAT | TTTAAGTTCT | AGTAACCTCC | 1620
| AGTGCTATTG | TTTCTCTAGG | TTTCGGTGGA | CCGGGTCTTA | AAGACCCTGA | AAGAAAACGC | 1680
| TAATAAAGCC | AAAAGCTTAC | TGCTCACTAC | CATACCTCAG | ATAGGGTCCA | CAGAATGGTC | 1740
| AGAAACCCTC | CATAACCTGA | AGGTAAGTGC | AGCCATGGAC | AATCAGGCAT | GTCTGTAGAC | 1800
| TCTCTATTGT | CTTCTTTTCT | TACTTGCATT | TCACCTTTGG | TCCTCATGTA | TTTTTTGCCA | 1860
| GCCTAGATGT | TTTCAACAAG | TTTTTGTGAC | ATCTACTACT | ACCATACCAA | CCACTTGTGA | 1920
| AACTGAGTAG | TCTTATTTTC | TTGGCTGGTA | GTGCAGANNN | NNNNNNNNNN | NNAATAAACA | 1980
| ATAATCCAGG | CTGGGCTGGT | ATGGCAATAA | GTGATTATCA | GAACAATGCT | CTGAGATAAG | 2040
| CATTATTAAC | CTCACTTTAC | AGGAAAGGGA | GGTGAGGAAC | CAAGAGTTTA | GAGTACCCGA | 2100
| AGTTCCACAT | CTGGTTAGTG | AACTTGAAAA | TTTTCTGTAG | AATTTATTTA | AAGTGTATGT | 2160
| TTCCTGCGTC | CTCACTTTGA | TCTAGAAAAT | CAAAATCTGT | TTTTTTTTT | AACAAACATC | 2220
| TCAGTAATTA | CGCCAACATG | TGAATATCAC | TGCCTCCTTT | CTTCCTTTCA | GAATATGGCC | 2280
| CAGTTTTCTG | TTTTATTACC | AAGACATTAA | AGTAGCATGG | CTGCCCAGGA | GAAAAGAAGA | 2340
| CATTCTAATT | CCAGTCATTT | TGGGAATTCC | TGCTTAACTT | GAAAAAAATA | TGGGAAAGAC | 2400
| ATGCAGCTTT | CATGCCCTTG | CCTATCAAAG | AGTATGTTGT | AAGAAAGACA | AGACATTGTG | 2460
| TGTATAGAGA | CTCCTCAATG | ATTTAGACAA | CTTCAAAATA | CAGAAGAAAA | GCAAATGACT | 2520
| AGTAACATGT | GGGAAAAAAT | ATTACATTTT | AAGGGGGAAA | AAAACCCCA | CCATTCTCTT | 2580
| CTCCCCCTAT | TAAATTTGCA | ACAATAAAGG | GTGGAGGGTA | ATCTCTACTT | TCCTATACTG | 2640
| CCAAAGAATG | TGAGGAAGAA | ATGGGACTCT | TTGGTTATTT | ATTGATGCGA | CTGTAAATTG | 2700
| GTACAGTATT | TCTGGAGGGC | AATTTGGTAA | AATGCATCAA | AAGACTTAAA | AATACGGACG | 2760
| TAC | | | | | | 2763

( 2 ) INFORMATION FOR SEQ ID NO:2:

( i ) SEQUENCE CHARACTERISTICS:
        ( A ) LENGTH: 17 amino acids

```
            ( B ) TYPE: amino acid
            ( C ) STRANDEDNESS: single
            ( D ) TOPOLOGY: linear ( i i ) MOLECULE TYPE: peptide ( v i i ) IMMEDIATE SOURCE:
            ( B ) CLONE: methyladenosine phosphatase peptides ( i x ) FEATURE:
            ( A ) NAME/KEY: Peptide
            ( B ) LOCATION: 1..17

( x i ) SEQUENCE DESCRIPTION: SEQ ID NO:2:

Ile Gly Ile Ile Gly Gly Thr Gly Leu Asp Asp Pro Glu Ile Leu Glu
    1               5                   10                  15

Gly ( 2 ) INFORMATION FOR SEQ ID NO:3:

( i ) SEQUENCE CHARACTERISTICS:
            ( A ) LENGTH: 13 amino acids
            ( B ) TYPE: amino acid
            ( C ) STRANDEDNESS: single
            ( D ) TOPOLOGY: linear ( i i ) MOLECULE TYPE: peptide ( v i i ) IMMEDIATE SOURCE:
            ( B ) CLONE: methyladenosine phosphatase peptides ( i x ) FEATURE:
            ( A ) NAME/KEY: Peptide
            ( B ) LOCATION: 1..13

( x i ) SEQUENCE DESCRIPTION: SEQ ID NO:3:

Leu Leu Leu Thr Thr Ile Pro Gln Ile Gly Ser Met Glu
    1               5                   10

( 2 ) INFORMATION FOR SEQ ID NO:4:

( i ) SEQUENCE CHARACTERISTICS:
            ( A ) LENGTH: 1615 base pairs
            ( B ) TYPE: nucleic acid
            ( C ) STRANDEDNESS: single
            ( D ) TOPOLOGY: linear ( i i ) MOLECULE TYPE: DNA (genomic)

( v i i ) IMMEDIATE SOURCE:
            ( B ) CLONE: methionine-gamma- lyase ( i x ) FEATURE:
            ( A ) NAME/KEY: CDS
            ( B ) LOCATION: 304..1497

( x i ) SEQUENCE DESCRIPTION: SEQ ID NO:4:
```

| | | | | | |
|---|---|---|---|---|---|
| ATAGGATGGC | CTGGTAGCCA | GTGATATAGC | CGTTGTCTTC | CAGCAGCTTG | ACCCGGCGCC    60 |
| AGCAGGGGCG | AGGTGGTCAA | TGCCACCTGG | TCGGCAAGTT | CGGCGACGGT | TAGGCGGGCG   120 |
| TTGTCCTGCA | AGGCGGCGAG | CAGGGCGCGG | TCGGTGCGGT | CGAGGCTTGA | AGGCATGTTT   180 |
| TGCCCTCCTG | GTCCGTTAAT | TATTGTTTTT | GTTCCAGCAA | GCACGCAGAT | GCGTGGGCAA   240 |
| TTTTGGAAAA | AATCGGGCAG | CTCGGTGGCA | TAAGCTTATA | ACAAACCACA | AGAGGCTGTT   300 |

```
GCC ATG CGC GAC TCC CAT AAC AAC ACC GGT TTT TCC ACA CGG GCC ATT        348
    Met Arg Asp Ser His Asn Asn Thr Gly Phe Ser Thr Arg Ala Ile
    1               5                   10                  15

CAC CAC GGC TAC GAC CCG CTT TCC CAC GGT GGT GCC TTG GTG CCA CCG        396
His His Gly Tyr Asp Pro Leu Ser His Gly Gly Ala Leu Val Pro Pro
                20                  25                  30
```

| | | | | | | | | | | | | | | | |
|---|---|---|---|---|---|---|---|---|---|---|---|---|---|---|---|
| GTG | TAC | CAG | ACC | GCG | ACC | TAT | GCC | TTC | CCG | ACT | GTC | GAA | TAC | GGC | GCT |
| Val | Tyr | Gln | Thr | Ala | Thr | Tyr | Ala | Phe | Pro | Thr | Val | Glu | Tyr | Gly | Ala |
| | | | 35 | | | | 40 | | | | | | 45 | | |

444

| GCG | TGC | TTC | GCC | GGG | GAG | GAG | GCG | GGG | CAC | TTC | TAC | AGC | CGC | ATC | TCC |
|---|---|---|---|---|---|---|---|---|---|---|---|---|---|---|---|
| Ala | Cys | Phe | Ala | Gly | Glu | Glu | Ala | Gly | His | Phe | Tyr | Ser | Arg | Ile | Ser |
| | | 50 | | | | | 55 | | | | | 60 | | | |

492

| AAC | CCC | ACC | CTG | GCC | TTG | CTC | GAG | CAA | CGC | ATG | GCC | TCG | TTG | GAG | GGT |
|---|---|---|---|---|---|---|---|---|---|---|---|---|---|---|---|
| Asn | Pro | Thr | Leu | Ala | Leu | Leu | Glu | Gln | Arg | Met | Ala | Ser | Leu | Glu | Gly |
| 65 | | | | | 70 | | | | | 75 | | | | | |

540

| GGT | GAG | GCG | GGA | TTG | GCG | CTG | GCG | TCG | GGG | ATG | GGA | GCC | ATT | ACT | TCG |
|---|---|---|---|---|---|---|---|---|---|---|---|---|---|---|---|
| Gly | Glu | Ala | Gly | Leu | Ala | Leu | Ala | Ser | Gly | Met | Gly | Ala | Ile | Thr | Ser |
| 80 | | | | | 85 | | | | | 90 | | | | | 95 |

588

| ACC | CTC | TGG | ACC | CTG | CTG | CGG | CCT | GGT | GAT | GAG | CTG | ATC | GTG | GGG | CGC |
|---|---|---|---|---|---|---|---|---|---|---|---|---|---|---|---|
| Thr | Leu | Trp | Thr | Leu | Leu | Arg | Pro | Gly | Asp | Glu | Leu | Ile | Val | Gly | Arg |
| | | | 100 | | | | | 105 | | | | | 110 | | |

636

| ACC | TTG | TAT | GGC | TGC | ACC | TTT | GCG | TTC | CTG | CAC | CAT | GGC | ATT | GGC | GAG |
|---|---|---|---|---|---|---|---|---|---|---|---|---|---|---|---|
| Thr | Leu | Tyr | Gly | Cys | Thr | Phe | Ala | Phe | Leu | His | His | Gly | Ile | Gly | Glu |
| | | | 115 | | | | 120 | | | | | 125 | | | |

684

| TTC | GGG | GTC | AAG | ATC | CAC | CAT | GTC | GAC | CTT | AAC | GAT | GCC | AAG | GCC | CTG |
|---|---|---|---|---|---|---|---|---|---|---|---|---|---|---|---|
| Phe | Gly | Val | Lys | Ile | His | His | Val | Asp | Leu | Asn | Asp | Ala | Lys | Ala | Leu |
| | | 130 | | | | | 135 | | | | | 140 | | | |

732

| AAA | GCG | GCG | ATC | AAC | AGC | AAA | ACG | CGG | ATG | ATC | TAC | TTC | GAA | ACA | CCG |
|---|---|---|---|---|---|---|---|---|---|---|---|---|---|---|---|
| Lys | Ala | Ala | Ile | Asn | Ser | Lys | Thr | Arg | Met | Ile | Tyr | Phe | Glu | Thr | Pro |
| 145 | | | | | 150 | | | | | 155 | | | | | |

780

| GCC | AAC | CCC | AAC | ATG | CAA | CTG | GTG | GAT | ATA | GCG | GCG | GTC | GTC | GAG | GCA |
|---|---|---|---|---|---|---|---|---|---|---|---|---|---|---|---|
| Ala | Asn | Pro | Asn | Met | Gln | Leu | Val | Asp | Ile | Ala | Ala | Val | Val | Glu | Ala |
| 160 | | | | | 165 | | | | | 170 | | | | | 175 |

828

| GTG | CGG | GGG | AGT | GAT | GTG | CTT | GTG | GTG | GTC | GAC | AAC | ACC | TAC | TGC | ACG |
|---|---|---|---|---|---|---|---|---|---|---|---|---|---|---|---|
| Val | Arg | Gly | Ser | Asp | Val | Leu | Val | Val | Val | Asp | Asn | Thr | Tyr | Cys | Thr |
| | | | 180 | | | | | 185 | | | | | 190 | | |

876

| CCC | TAC | CTG | CAG | CGG | CCA | CTG | GAA | CTG | GGG | GCA | GAC | CTG | GTG | GTG | CAT |
|---|---|---|---|---|---|---|---|---|---|---|---|---|---|---|---|
| Pro | Tyr | Leu | Gln | Arg | Pro | Leu | Glu | Leu | Gly | Ala | Asp | Leu | Val | Val | His |
| | | | 195 | | | | | 200 | | | | | 205 | | |

924

| TCG | GCA | ACC | AAG | TAC | CTC | AGT | GGC | CAT | GGC | GAC | ATC | ACT | GCG | GGC | CTG |
|---|---|---|---|---|---|---|---|---|---|---|---|---|---|---|---|
| Ser | Ala | Thr | Lys | Tyr | Leu | Ser | Gly | His | Gly | Asp | Ile | Thr | Ala | Gly | Leu |
| | | | 210 | | | | | 215 | | | | | 220 | | |

972

| GTG | GTG | GGG | CGC | AAG | GCT | TTG | GTC | GAC | CGC | ATT | CGG | CTG | GAA | GGG | CTG |
|---|---|---|---|---|---|---|---|---|---|---|---|---|---|---|---|
| Val | Val | Gly | Arg | Lys | Ala | Leu | Val | Asp | Arg | Ile | Arg | Leu | Glu | Gly | Leu |
| 225 | | | | | 230 | | | | | 235 | | | | | |

1020

| AAA | GAC | ATG | ACC | GGG | GCA | GCC | TTG | TCA | CCG | CAT | GAC | GCT | GCG | TTG | TTG |
|---|---|---|---|---|---|---|---|---|---|---|---|---|---|---|---|
| Lys | Asp | Met | Thr | Gly | Ala | Ala | Leu | Ser | Pro | His | Asp | Ala | Ala | Leu | Leu |
| 240 | | | | | 245 | | | | | 250 | | | | | 255 |

1068

| ATG | CGC | GGC | ATC | AAG | ACC | CTG | GCG | CTG | CGC | ATG | GAC | CGG | CAT | TGC | GCC |
|---|---|---|---|---|---|---|---|---|---|---|---|---|---|---|---|
| Met | Arg | Gly | Ile | Lys | Thr | Leu | Ala | Leu | Arg | Met | Asp | Arg | His | Cys | Ala |
| | | | | 260 | | | | | 265 | | | | | 270 | |

1116

| AAC | GCC | CTG | GAG | GTC | GCG | CAG | TTC | CTG | GCC | GGG | CAG | CCC | CAG | GTG | GAG |
|---|---|---|---|---|---|---|---|---|---|---|---|---|---|---|---|
| Asn | Ala | Leu | Glu | Val | Ala | Gln | Phe | Leu | Ala | Gly | Gln | Pro | Gln | Val | Glu |
| | | | 275 | | | | | 280 | | | | | 285 | | |

1164

| CTG | ATC | CAC | TAC | CCG | GGC | TTG | CCG | TCG | TTT | GCC | CAG | TAC | GAA | CTG | GCA |
|---|---|---|---|---|---|---|---|---|---|---|---|---|---|---|---|
| Leu | Ile | His | Tyr | Pro | Gly | Leu | Pro | Ser | Phe | Ala | Gln | Tyr | Glu | Leu | Ala |
| | | 290 | | | | | 295 | | | | | 300 | | | |

1212

| CAG | CGG | CAG | ATG | CGT | TTG | CCG | GGC | GGG | ATG | ATT | GCC | TTT | GAG | CTC | AAG |
|---|---|---|---|---|---|---|---|---|---|---|---|---|---|---|---|
| Gln | Arg | Gln | Met | Arg | Leu | Pro | Gly | Gly | Met | Ile | Ala | Phe | Glu | Leu | Lys |
| | 305 | | | | | 310 | | | | | 315 | | | | |

1260

| GGC | GGT | ATC | GAG | GCC | GGG | CGC | GGC | TTC | ATG | AAT | GCC | CTG | CAG | CTT | TTT |
|---|---|---|---|---|---|---|---|---|---|---|---|---|---|---|---|
| Gly | Gly | Ile | Glu | Ala | Gly | Arg | Gly | Phe | Met | Asn | Ala | Leu | Gln | Leu | Phe |
| 320 | | | | | 325 | | | | | 330 | | | | | 335 |

1308

| GCC | CGT | GCG | GTG | AGC | CTG | GGG | GAT | GCC | GAG | TCG | CTG | GCA | CAG | CAC | CCG |
|---|---|---|---|---|---|---|---|---|---|---|---|---|---|---|---|
| Ala | Arg | Ala | Val | Ser | Leu | Gly | Asp | Ala | Glu | Ser | Leu | Ala | Gln | His | Pro |
| | | | | 340 | | | | | 345 | | | | | 350 | |

1356

| | | | | | | | | | | | | | | | |
|---|---|---|---|---|---|---|---|---|---|---|---|---|---|---|---|
| GCG | AGC | ATG | ACG | CAC | TCC | AGT | TAC | ACG | CCA | CAA | GAG | CGG | GCG | CAT | CAC |
| Ala | Ser | Met | Thr | His | Ser | Ser | Tyr | Thr | Pro | Gln | Glu | Arg | Ala | His | His |
| | | 355 | | | | | | 360 | | | | | 365 | | |

1404

| | | | | | | | | | | | | | | | |
|---|---|---|---|---|---|---|---|---|---|---|---|---|---|---|---|
| GGG | ATA | TCA | GAG | GGG | CTG | GTG | AGG | TTG | TCA | GTG | GGG | CTG | GAG | GAT | GTG |
| Gly | Ile | Ser | Glu | Gly | Leu | Val | Arg | Leu | Ser | Val | Gly | Leu | Glu | Asp | Val |
| | | 370 | | | | | 375 | | | | | 380 | | | |

1452

| | | | | | | | | | | | | | |
|---|---|---|---|---|---|---|---|---|---|---|---|---|---|
| GAG | GAC | CTG | CTG | GCA | GAT | ATC | GAG | TTG | GCG | TTG | GAG | GCG | TGT | GCA |
| Glu | Asp | Leu | Leu | Ala | Asp | Ile | Glu | Leu | Ala | Leu | Glu | Ala | Cys | Ala |
| | 385 | | | | | 390 | | | | | 395 | | | |

1497

TGAACTTGCC TTGCAGGATC GGGAACACTT GCCCAATGCC TCACGGGATC AGGCGATGGC    1557

ACTTTGGATG AGCTGGTGAA TTGGCCGGCT TATCCAAGAG GAGTTTAAAA TGACCGTA      1615

( 2 ) INFORMATION FOR SEQ ID NO:5:

( i ) SEQUENCE CHARACTERISTICS:
        ( A ) LENGTH: 398 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Arg | Asp | Ser | His | Asn | Asn | Thr | Gly | Phe | Ser | Thr | Arg | Ala | Ile | His |
|---|---|---|---|---|---|---|---|---|---|---|---|---|---|---|---|
| 1 | | | | 5 | | | | 10 | | | | | | 15 | |
| His | Gly | Tyr | Asp | Pro | Leu | Ser | His | Gly | Gly | Ala | Leu | Val | Pro | Pro | Val |
| | | | 20 | | | | | 25 | | | | | 30 | | |
| Tyr | Gln | Thr | Ala | Thr | Tyr | Ala | Phe | Pro | Thr | Val | Glu | Tyr | Gly | Ala | Ala |
| | | 35 | | | | | 40 | | | | | 45 | | | |
| Cys | Phe | Ala | Gly | Glu | Glu | Ala | Gly | His | Phe | Tyr | Ser | Arg | Ile | Ser | Asn |
| | 50 | | | | | 55 | | | | | 60 | | | | |
| Pro | Thr | Leu | Ala | Leu | Leu | Glu | Gln | Arg | Met | Ala | Ser | Leu | Glu | Gly | Gly |
| 65 | | | | | 70 | | | | | 75 | | | | | 80 |
| Glu | Ala | Gly | Leu | Ala | Leu | Ala | Ser | Gly | Met | Gly | Ala | Ile | Thr | Ser | Thr |
| | | | | 85 | | | | | 90 | | | | | 95 | |
| Leu | Trp | Thr | Leu | Leu | Arg | Pro | Gly | Asp | Glu | Leu | Ile | Val | Gly | Arg | Thr |
| | | | 100 | | | | | 105 | | | | | 110 | | |
| Leu | Tyr | Gly | Cys | Thr | Phe | Ala | Phe | Leu | His | His | Gly | Ile | Gly | Glu | Phe |
| | | 115 | | | | | 120 | | | | | 125 | | | |
| Gly | Val | Lys | Ile | His | His | Val | Asp | Leu | Asn | Asp | Ala | Lys | Ala | Leu | Lys |
| | 130 | | | | | 135 | | | | | 140 | | | | |
| Ala | Ala | Ile | Asn | Ser | Lys | Thr | Arg | Met | Ile | Tyr | Phe | Glu | Thr | Pro | Ala |
| 145 | | | | | 150 | | | | | 155 | | | | | 160 |
| Asn | Pro | Asn | Met | Gln | Leu | Val | Asp | Ile | Ala | Ala | Val | Val | Glu | Ala | Val |
| | | | 165 | | | | | 170 | | | | | 175 | | |
| Arg | Gly | Ser | Asp | Val | Leu | Val | Val | Asp | Asn | Thr | Tyr | Cys | Thr | Pro |
| | | | 180 | | | | | 185 | | | | | 190 | | |
| Tyr | Leu | Gln | Arg | Pro | Leu | Glu | Leu | Gly | Ala | Asp | Leu | Val | Val | His | Ser |
| | | 195 | | | | | 200 | | | | | 205 | | | |
| Ala | Thr | Lys | Tyr | Leu | Ser | Gly | His | Gly | Asp | Ile | Thr | Ala | Gly | Leu | Val |
| | 210 | | | | | 215 | | | | | 220 | | | | |
| Val | Gly | Arg | Lys | Ala | Leu | Val | Asp | Arg | Ile | Arg | Leu | Glu | Gly | Leu | Lys |
| 225 | | | | | 230 | | | | | 235 | | | | | 240 |
| Asp | Met | Thr | Gly | Ala | Ala | Leu | Ser | Pro | His | Asp | Ala | Ala | Leu | Leu | Met |
| | | | | 245 | | | | | 250 | | | | | 255 | |
| Arg | Gly | Ile | Lys | Thr | Leu | Ala | Leu | Arg | Met | Asp | Arg | His | Cys | Ala | Asn |
| | | | | | | | | | 265 | | | | 270 | | |

| Ala | Leu | Glu | Val | Ala | Gln | Phe | Leu | Ala | Gly | Gln | Pro | Gln | Val | Glu | Leu |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |
| Ile | His | Tyr | Pro | Gly | Leu | Pro | Ser | Phe | Ala | Gln | Tyr | Glu | Leu | Ala | Gln |
|     | 290 |     |     |     |     | 295 |     |     |     |     | 300 |     |     |     |     |
| Arg | Gln | Met | Arg | Leu | Pro | Gly | Gly | Met | Ile | Ala | Phe | Glu | Leu | Lys | Gly |
| 305 |     |     |     |     | 310 |     |     |     |     | 315 |     |     |     |     | 320 |
| Gly | Ile | Glu | Ala | Gly | Arg | Gly | Phe | Met | Asn | Ala | Leu | Gln | Leu | Phe | Ala |
|     |     |     |     | 325 |     |     |     |     | 330 |     |     |     |     | 335 |     |
| Arg | Ala | Val | Ser | Leu | Gly | Asp | Ala | Glu | Ser | Leu | Ala | Gln | His | Pro | Ala |
|     |     |     | 340 |     |     |     |     | 345 |     |     |     |     | 350 |     |     |
| Ser | Met | Thr | His | Ser | Ser | Tyr | Thr | Pro | Gln | Glu | Arg | Ala | His | His | Gly |
|     |     | 355 |     |     |     |     | 360 |     |     |     |     | 365 |     |     |     |
| Ile | Ser | Glu | Gly | Leu | Val | Arg | Leu | Ser | Val | Gly | Leu | Glu | Asp | Val | Glu |
|     | 370 |     |     |     |     | 375 |     |     |     |     | 380 |     |     |     |     |
| Asp | Leu | Leu | Ala | Asp | Ile | Glu | Leu | Ala | Leu | Glu | Ala | Cys | Ala |     |     |
| 385 |     |     |     |     | 390 |     |     |     |     | 395 |     |     |     |     |     |